US009188543B2

(12) United States Patent
Li et al.

(10) Patent No.: US 9,188,543 B2
(45) Date of Patent: Nov. 17, 2015

(54) INSPECTION DEVICE AND METHOD THEREOF

(75) Inventors: Tao Li, Shanghai (CN); Guiju Song, Shanghai (CN); Kevin George Harding, Niskayuna, NY (US); Dongmin Yang, Skaneateles, NY (US); Zirong Zhai, Shanghai (CN); Jie Han, Shanghai (CN); Gil Abramovich, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 510 days.

(21) Appl. No.: 13/448,691

(22) Filed: Apr. 17, 2012

(65) Prior Publication Data

US 2013/0271763 A1 Oct. 17, 2013

(30) Foreign Application Priority Data

Apr. 18, 2011 (CN) .......................... 2011 1 0096267

(51) Int. Cl.
*G01N 21/88* (2006.01)
*G02B 26/00* (2006.01)
*G02B 27/28* (2006.01)
*G01N 21/21* (2006.01)

(52) U.S. Cl.
CPC ........ *G01N 21/8806* (2013.01); *G01N 21/8803* (2013.01); *G02B 26/00* (2013.01); *G02B 27/286* (2013.01); *G01N 21/21* (2013.01)

(58) Field of Classification Search
None
See application file for complete search history.

(56) References Cited

U.S. PATENT DOCUMENTS

| | | | | |
|---|---|---|---|---|
| 3,587,431 A | * | 6/1971 | Holler | 396/147 |
| 4,107,520 A | * | 8/1978 | Wilwerding | 250/201.8 |
| 4,211,472 A | | 7/1980 | Nakamura | |
| 4,783,152 A | * | 11/1988 | Nishimoto | 359/319 |
| 4,973,143 A | * | 11/1990 | Ishii et al. | 359/676 |
| 5,012,272 A | * | 4/1991 | Tabata et al. | 396/284 |
| 5,148,502 A | | 9/1992 | Tsujiuchi et al. | |

(Continued)

FOREIGN PATENT DOCUMENTS

| CN | 1841030 A | 10/2006 |
|---|---|---|
| CN | 101196468 A | 6/2008 |

(Continued)

OTHER PUBLICATIONS

Search Report and Written Opinion from EP Application No. 12164342.3 dated Aug. 20, 2012.

(Continued)

*Primary Examiner* — Gordon J Stock, Jr.
(74) *Attorney, Agent, or Firm* — GE Global Patent Operation (57) ABSTRACT

An optical system configured to visually inspect a target having a variable position with respect to the optical system is provided. The optical system includes a polarizer configured to convert an incident light reflected or diffused from the target into linearly polarized light; a light modulating element configured to modulate a polarization state of the linearly polarized light in response to control signals; and a lens group comprising at least one birefringent element, the birefringent element configured to refract or reflect the modulated linearly polarized light with a first polarization state under a first refraction index to enable inspection of the target at a first object position, and the birefringent element further configured to refract or reflect the modulated linearly polarized light with a second polarization state under a second refraction index to enable inspection of the target at a second object position.

16 Claims, 9 Drawing Sheets

(56) References Cited

U.S. PATENT DOCUMENTS

| | | | | |
|---|---|---|---|---|
| 6,148,113 | A * | 11/2000 | Wolverton et al. | 382/255 |
| 6,191,761 | B1 * | 2/2001 | Melville et al. | 345/32 |
| 6,288,767 | B1 * | 9/2001 | Murata et al. | 349/200 |
| 7,636,204 | B1 * | 12/2009 | Bourget | 359/726 |
| 2003/0050533 | A1 | 3/2003 | Minami | |
| 2006/0126054 | A1 * | 6/2006 | Kamon et al. | 356/5.07 |
| 2006/0238759 | A1 | 10/2006 | Okabe et al. | |
| 2009/0174918 | A1 * | 7/2009 | Zhuang et al. | 359/19 |
| 2009/0273703 | A1 * | 11/2009 | Kawauchi | 348/347 |
| 2013/0278740 | A1 * | 10/2013 | Zalevsky et al. | 348/76 |

FOREIGN PATENT DOCUMENTS

| | | |
|---|---|---|
| CN | 101893548 A | 11/2010 |
| GB | 1252276 A | 11/1971 |
| GB | 2403815 A | 1/2005 |
| JP | 8136832 A | 5/1996 |

OTHER PUBLICATIONS

Unofficial English translation of CN Office Action dated Dec. 10, 2013, issued in connection with corresponding CN Application No. 201110096267.1.

* cited by examiner

INSPECTION DEVICE AND METHOD THEREOF

BACKGROUND OF THE INVENTION

1. Field of the Invention

The field of the invention relates to inspection devices. More particularly, to an inspection device having the capability of inspecting a target having variable positions with respect to the inspection device.

2. Description of Related Art

Inspection devices including borescopes, videoscopes, fiberscopes, and endoscopes are non-destructive evaluation (NDE) tools widely used in industrial applications and medical applications. The inspection devices are often used to inspect inaccessible locations for damage or wear or to verify whether parts have been properly manufactured or assembled. The inspection devices may employ an external light source coupled to fiber optic bundles or a light source, such as LED, placed at the device's distal end to provide illumination of a target. When the target is illuminated, an image of the target is formed by a lens system on an image sensor, and the image is relayed to a display such as a video screen. In order to inspect a large range of field, the lens system in front of the image sensor with a fixed focal length needs to be designed to achieve a large depth of field (DOF). However, a larger DOF lens will result in a darker image due to smaller aperture stop used. Such darker images may result in inspection failures or difficulties. Typically, a set of a variety DOF tips with different lenses are used in inspection devices with some tips offering near field inspection and the other tips being used for mid to far field inspection. However, repeatedly changing the tips is time-consuming and may decrease the inspection efficiency and user convenience.

Therefore, it is desirable to provide an inspection device and method of operating the inspection device to address the above-mentioned problems.

BRIEF SUMMARY OF THE INVENTION

According to an embodiment of the present invention an optical system configured to visually inspect a target is provided. The target comprising variable positions with respect to the optical system. The optical system comprising a polarizer configured to convert an incident light reflected or diffused from the target into linearly polarized light; a light modulating element configured to modulate a polarization state of the linearly polarized light in response to control signals; and a lens group comprising at least one birefringent element, the birefringent element configured to refract or reflect the modulated linearly polarized light with a first polarization state under a first refraction index to enable inspection of the target at a first object position with respect to the optical system, and the birefringent element further configured to refract or reflect the modulated linearly polarized light with a second polarization state under a second refraction index to enable inspection of the target at a second object position with respect to the optical system.

According to another embodiment of the present invention an inspection device for inspecting at least a near field target and a far field target is also provided. The inspection device comprises a light source and an optical system, wherein the light source is configured to emit light to illuminate the near field target or the far field target; and an optical system is configured for receiving light reflected or diffused from the near field target or the far field target, convert the reflected or diffused light to linearly polarized light, modulate a polarization state of the linearly polarized light, and refract or reflect the modulated linearly polarized light under either a first refractive power when the near field target is to be inspected or a second refractive power when the far field target is to be inspected.

According to another embodiment of the present invention a method for inspecting a target, wherein the target comprises variable positions with respect to an optical system employed in an inspection device, is further provided. The method comprises receiving light reflected or diffused from the target; converting the received light into a linearly polarized light; modulating a polarization state of the linearly polarized light in response to control signals; and refracting or reflecting the modulated linearly polarized light using at least one refractive element, wherein the at least one refractive element is configured to refract different polarization states under different refractive indices.

According to another embodiment of the present invention an optical system configured to visually inspect a target by converging light reflected or diffused from the target to an imager is provided. The optical system comprises a polarizer configured to convert the light reflected or diffused from the target to a linearly polarized light; a light modulating element configured to selectively modulate the linearly polarized light; and a lens group configured to converge a first polarized light and a second polarized light modulated by the light modulating element to the imager, the lens group comprising at least one birefringent element, the birefringent element configured to refract the first polarized light under a first focal length to form a first image of the target on the imager, and the birefringent element further configured to refract the second polarized light under a second focal length to form a second image of the target on the imager, wherein the second image is zoomed in a ratio with respect to the first image, and the ratio is determined based at least on the first focal length and the second focal length.

BRIEF DESCRIPTION OF THE SEVERAL VIEWS OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION OF THE INVENTION

Embodiments disclosed herein relate to an inspection device and a method of using the inspection device for visually inspecting a target having variable positions with respect to the inspection device. This is achieved by designing an optical system in the inspection device with the capability of focusing light with at least two focal lengths.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect.

Figure 1:
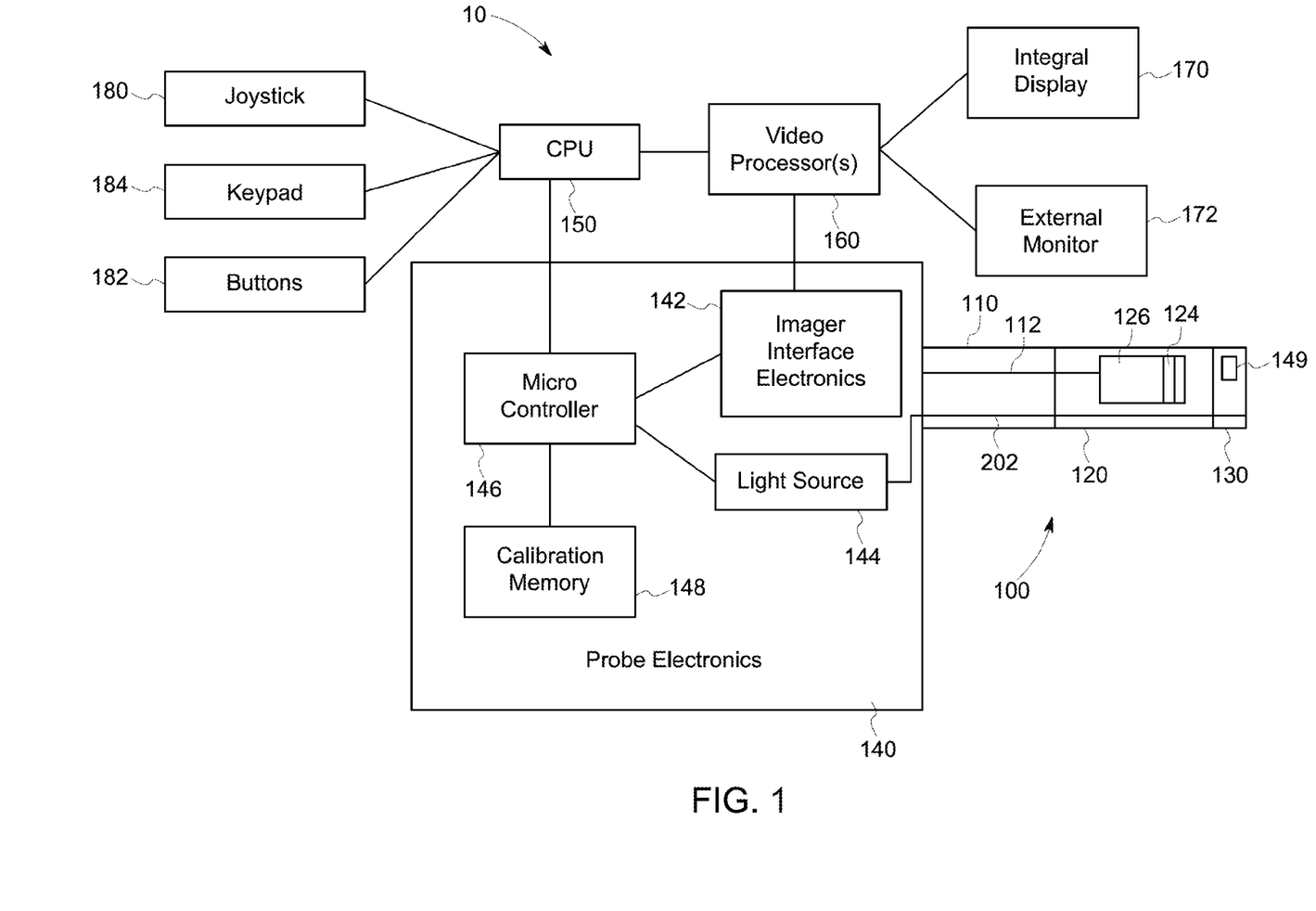
FIG. 1 is a block diagram of an inspection device in accordance with an exemplary embodiment of the present disclosure.

FIG. 1 illustrates a block diagram of an inspection device 10 in accordance with an exemplary embodiment. The inspection device 10 may comprise a device such as a borescope, a videoscope, a fiberscope, or an endoscope, for example, and may be used in applications such as industrial applications and medical applications. In one implementation, the inspection device 10 may be used for remote visual inspection in a hard-to-access area. Data obtained by the inspection device may be used for condition monitoring and detection of defects such as edge breaks, scratches, and surface finish pits, for example.

Referring to FIG. 1, the inspection device 10 may include an elongated probe 100 comprising an insertion tube 110 and a head assembly 120 disposed at the distal end of the insertion tube 110. The insertion tube 110 may be a flexible, tubular section through which all interconnects between the head assembly 120 and probe electronics 140 are passed. The elongated probe 100 may include an optical system 130 (or "tip") for guiding and focusing light reflected or diffused from the target onto an imager 124. The light reflected or diffused from the target may be generated from a light source 144 and may be transmitted through a fiber optic bundle 202. The light source 144 may comprise a white light source and may comprise any appropriate light source for a probe such as a mercury or metal halide arc lamp, halogen lamp, laser/phosphor system, or LED based light source, for example.

The imager 124 may include a plurality of pixels formed in a plurality of rows and columns and is configured to generate image signals in the form of analog voltages representative of light incident on each pixel of the imager 124. In one embodiment, the image signals are then propagated through imager hybrid 126, which provides electronics for signal buffering and conditioning, to an imager harness 112, which provides wires for control and video signals between the imager hybrid 126 and the imager interface electronics 142. The imager interface electronics 142 can include power supplies, a timing generator for generating imager clock signals, an analog front end for digitizing the imager video output signal, and a digital signal processor for processing the digitized imager video data into a more useful video format.

The imager interface electronics 142 may optionally be included within the probe electronics 140, which provide a collection of functions for operating the inspection device 10. The probe electronics 140 may also include a calibration memory 148, which stores the calibration data for the probe 100. The microcontroller 146 may also be included in the probe electronics 140 for communicating with the imager interface electronics 142 for determining and setting gain and exposure settings, storing and reading calibration data from the calibration memory 148, controlling the light delivered to the target, and communicating with a CPU 150 of the inspection device 10.

In addition to communicating with the microcontroller 146, the imager interface electronics 142 can also communicate with one or more video processors 160. The video processor 160 can receive video signals from the imager interface electronics 142 and output signals to various monitors, including an integral display 170 or an external monitor 172. The integral display 170, in one embodiment, comprises an LCD screen built into the inspection device 10 for displaying various images or data (e.g., the image of the target, menus, cursors, measurement results) to an inspector. The external monitor 172 may comprise a video monitor or computer-type monitor connected to the inspection device 10 for displaying various images or data.

The video processor 160 may provide and receive commands, status information, streaming video, still video images, and graphical overlays to and from the CPU 150 and may be comprised of FPGAs, DSPs, or any other processing elements which provide functions such as image capture, image enhancement, graphical overlay merging, distortion correction, frame averaging, scaling, digital zooming, overlaying, merging, flipping, motion detection, and video format conversion and compression.

The CPU 150 may be used to manage the user interface by receiving input via a joystick 180, buttons 182, and/or keypad 184, in addition to providing a host of other functions, including image, video, and audio storage and recall functions, zoom and focus control, system control, and measurement processing.

The joystick 180 can be manipulated by the user to perform such operations as menu selection, cursor movement, slider adjustment, and articulation control of the probe 100, and may include a push-button function. The buttons 182 and/or keypad 184 also can be used for menu selection and providing user commands to the CPU 150 (e.g., freezing or saving a still video image).

Figure 2:
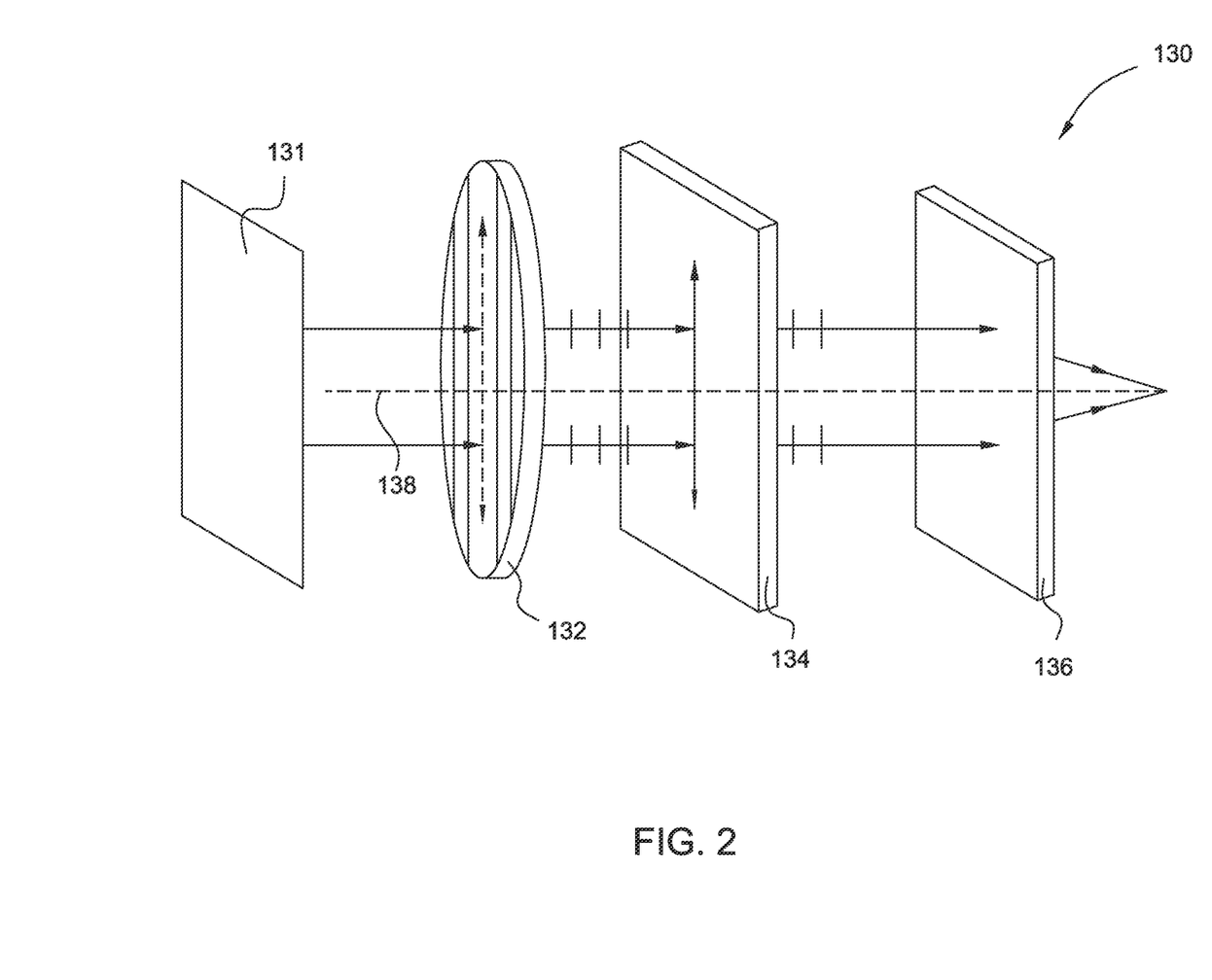
FIG. 2 is schematic illustrations of an optical system of the inspection device shown in FIG. 1 in accordance with an exemplary embodiment of the present disclosure, wherein the optical system is operated in a first focusing state for capturing images of a target in a near field.

FIG. 2 illustrates a perspective view of the optical system 130 shown in FIG. 1 in accordance with an exemplary embodiment. In one implementation, the optical system 130 may be removably mounted to the distal end of the head assembly 120 (shown in FIG. 1). In other implementations, the optical system 130 may be fixed to the head assembly 120. When the target 131 to be inspected varies its position, the optical system 130 is capable of being switched to converge light reflected or diffused from the target 131 with different focal lengths. Because the focal length of the optical system 130 will vary with respect to the birefringent element material's refractive index under different polarization state light, the optical system 130 can be switched to converge light with different refractive powers. Depending on the positions of the target 131 and the quality of the image formed by the converged light, the focal length of the optical system 130 may be manually switched or automatically switched, so that both a near field target and a far field target can be formed with clear images. As used herein, "near field" refers to a target having a relatively short distance with respect to an optical system. In one embodiment, as a non-limiting example, the near field may cover a range of 7 mm through 35 mm. As used herein, "far field" refers to the target having a relatively long distance with respect to an optical system. In one embodiment, as a non-limiting example, the far field may cover a range of 35 mm through 450 mm.

Referring to FIG. 2, in one embodiment, the optical system 130 comprises a polarizer 132, a light modulating element 134, and a lens group 136. In one implementation, as a non-limiting example, the polarizer 132, the light modulating element 134, and the lens group 136 are separately constructed in the optical system 130. In other implementations, two or more optical elements in the optical system 130 may be integrated together to form a single element. For example, in some embodiments, the polarizer 132 and the light modulating element 134 may be combined together. The polarizer 132, the light modulating element 134, and the lens group 136 are arranged substantially perpendicular to an optical axis 138. In some implementations, one or more optical elements may be further disposed between the polarizer 132 and the light modulating element 134, or between the light modulating element 134 and the lens group 136.

With continuing reference to FIG. 2, the polarizer 132 is used for converting incident light from the target 131 to be inspected to linearly polarized light. In one implementation, the polarizer 132 may generate the linearly polarized light based on an optical reflection mechanism. In this implementation, the polarizer 132 may be selected from a group consisting of a grating polarizer, a Glan-Taylor polarizer, a Glan-Thompson polarizer, and a piece stack polarizer, for example. In another implementation, the polarizer 132 may generate the linearly polarized light based on an optical refraction mechanism. In this implementation, the polarizer 132 may be selected from a group consisting of a Rochon polarizer and a Wollaston polarizer, for example. In yet another implementation, the polarizer 132 may generate the linearly polarized light based on an optical absorption mechanism. In this implementation, the polarizer 132 may comprise a polymer polarizing film, for example.

With continuing reference to FIG. 2, the light modulating element 134 is used for modulating or changing a polarization state of the linearly polarized light in response to controls signals. In one implementation, the light modulating element 134 may comprise liquid crystal. When a linearly polarized light passes through the light modulation element 134, a polarization state of the linearly polarized light can be changed by driving the liquid crystal with different voltages. For example, an incident light to the light modulating element 134 may be in vertical polarized state. When the liquid crystal is driven with a voltage of 0 volt, the emergent light from the light modulating element 134 is in vertical polarized state. When the liquid crystal is driven with a voltage larger than a threshold value, the emergent light from the light modulating element 134 is in horizontal polarized state. In other implementations, the light modulating element 134 may be not limited to liquid crystal. For example, a Faraday rotator, an optoelectric crystal, and a wave plate are other alternative elements which may be used to modulate the polarization state of incident light to the light modulating element 134.

With continuing reference to FIG. 2, in one implementation, the lens group 136 is used for converging light to an image plane, such that an image of the target 131 can be formed by the converged light. In one embodiment, the lens group 136 may include one or more birefringent lens(es), which can refract light of different polarization states under different refractive indexes correspondingly. In one implementation, the birefringent lens may use Yttrium orthovanadate (YVO4) to refract the light. YVO4 is a typical type of birefringent material, which can exhibit different refractive indexes with respect to incident light having different polarization states. For example, an un-polarized light incident to the YVO4 can be decomposed into extra-ordinary (e-beam) and ordinary (o-beam) light. In other implementations, the birefringent lens may use other materials such as α-BBO Crystal ($BaB_2O_4$), Calcite, Lithium Niobate, Quartz, or a combination of such materials.

Figure 3:
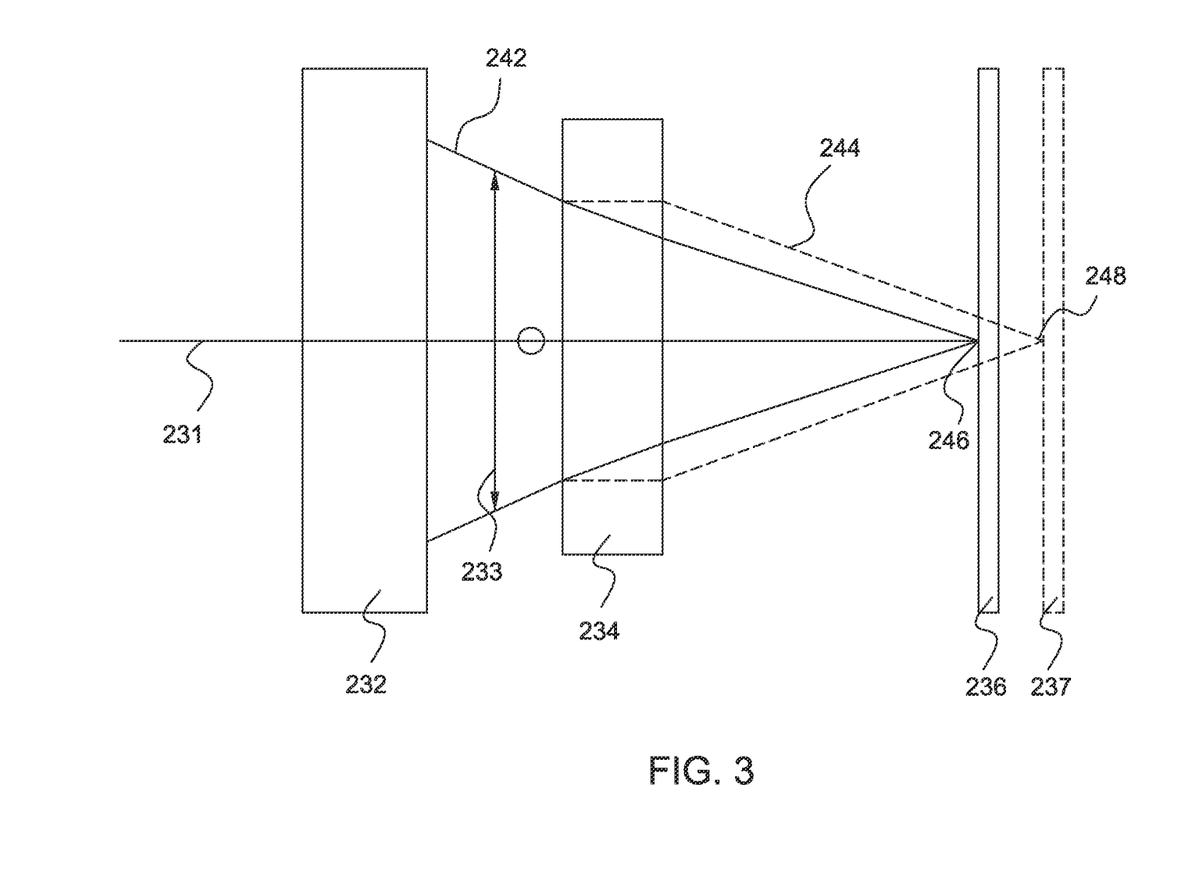
FIG. 3 illustrates an alternative embodiment of an optical system for shifting focal position in accordance with an exemplary embodiment.

In an alternative embodiment, the lens group 136 may comprise one or more birefringent window elements or one or more polarization splitting prism elements configured to create a different optical path length for different polarization state light. The change in optical path length by the birefringent window or polarization splitting prism elements has the effect on the focal position shifting of the lens group 136 or the optical system 130. Referring to FIG. 3, in one implementation, a birefringent window 234 in combination with a light modulating element 232 are illustrated for focal position shifting. As shown, the birefringent window 234 is placed between the light modulating element 232 and the imager 124 (shown in FIG. 1). In one implementation, the light modulating element 232 may comprise liquid crystal responsive to voltages for modulating the polarization state of incoming light reflected from or diffused from the target. The birefringent window 234 may comprise materials such as Yttrium orthovanadate (YVO4), α-BBO Crystal ($BaB_2O_4$), Calcite, Lithium Niobate, Quartz, or a combination of such materials. The birefringent window 234 is configured for refracting a first polarized state light 244 modulated by the light modulating element 232 to create a first imager focusing position 237 and form a first image of the target on the imager 124. The birefringent window 234 is further configured for refracting a second polarized state light 242 modulated by the light modulating element 232 to create a second imager focusing position 236 and form a second image of the target on the imager 124. Because the birefringent window 234 exhibits different refractive index with respect to the first polarized state light 244 and the second polarized state light 242, first imager focusing position 237 is shifted relative to the second imager focusing position 236 during switching operations.

In one implementation, the birefringent window 234 is cut with a fast axis 233 perpendicular to the optical axis 231. When the first polarized state light 244 modulated by the light modulating element 232 is polarized along the fast axis 233, the optical path through the birefringent window 234 is equal to L times $n_o$, where L refers to a thickness of the birefringent window 234, and $n_o$ refers to the refractive index of the birefringent window 234 for polarizations perpendicular (ordinary) to the axis of anisotropy. When the second polarized state light 242 modulated by the light modulating element 232 is polarized perpendicular to the fast axis 233, the optical path through the birefringent window 234 is equal to L times $n_e$, where $n_e$ refers to the refractive index of the birefringent window 234 for polarizations parallel (extraordinary) to the axis of anisotropy. In the case of YVO4, the refractive index shift between the two orientations is around 0.235 RIU (refractive index units). A birefringent window having a thickness of 0.5 millimeters can provide a change in optical path length about 0.12 millimeters and a focal position shift of 0.05 mm.

Referring again to FIG. 2, in operation, the optical system 130 may be operated to capture images of a target 131 in the near field. In this case, the optical system 130 may be switched to operate in a first focusing mode having a first focal length. The light source 144 shown in FIG. 1 may be switched on to emit light. The light may be transmitted directly or indirectly by fiber optic bundles to the target 131 so as to illuminate the target 131. The light reflected or diffused from the target 131 is converted to linearly polarized light by the polarizer 132. In one embodiment, the linearly polarized light comprises a vertical polarized light. The vertical polarized light emergent from the polarizer 132 is modulated by the light modulating element 134. In one implementation, the liquid crystal is applied with a voltage of 0 volts, and the light emergent from the light modulating element 134 continues to be vertical polarized light. The vertical polarized light passes through the lens group 136 and is converged to the imager 124 under a first refractive power, such that the image of the target 131 in the near field can be formed for inspection.

Figure 4:
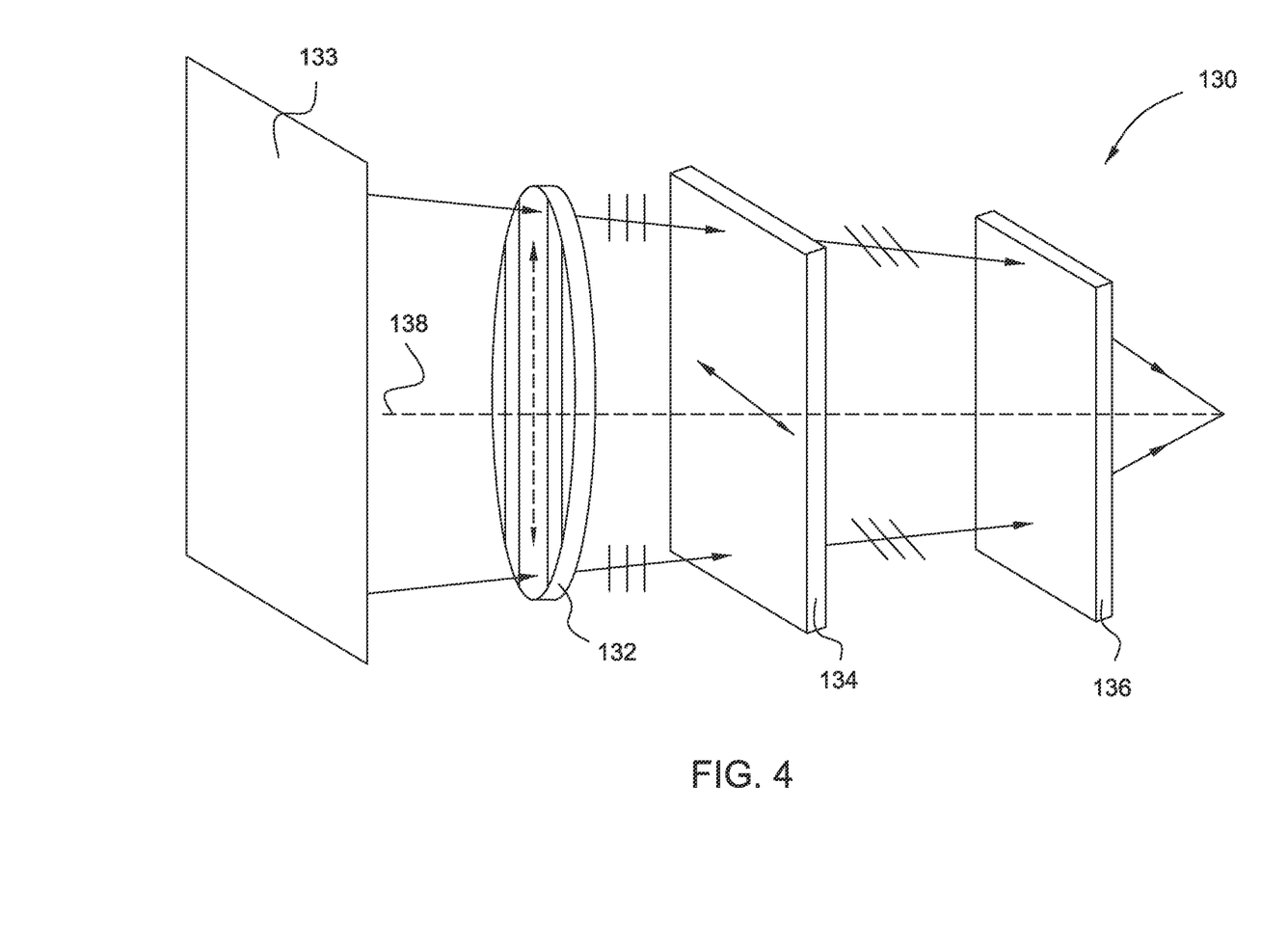
FIG. 4 illustrates the optical system shown in FIG. 2 operating in a second focusing state for capturing images of a target in a far field.

Referring to FIG. 4, in contrast, the optical system 130 may be further operated to capture images of a target 133 in the far field. In one implementation, the target 133 may be the same target 131 as is shown in FIG. 2. In other implementations, the target 133 can be different from the target 131. In this case, the optical system 130 may be switched to operate in a second focusing mode having a second focal length, where the second focal length is larger than the first focal length. In the second focusing mode, the liquid crystal of the light modulating element 134 is applied with a voltage larger than a threshold value, such that the emergent light from the polarizer 132 is modulated to be a horizontal polarization state. Because the birefringent element exhibits a second refractive index with respect to the horizontal polarized light, the horizontal polarized light is converged to the imager 124 under a second refractive power, such that the image of the target 133 in the far field can be formed for inspection.

As described above, the optical system 130 may be manually or automatically switched between a first focusing mode and a second focusing mode. With regard to automatically switching the optical system 130 between the dual-focus modes, in one implementation, the position of the target may be detected by a detecting device or detector 149. When the position of the target is detected and determined to be in the near field, the inspection device 1—can send control signals to switch the optical system 130 in the first focusing mode in which a relatively shorter focal length is used for converging light and obtaining the image of the target in the near field. When the position of the target is detected and determined to be in the far field, the inspection device 10 can send control signals to switch the optical system 130 in the second focusing mode in which a relatively longer focal length is used for converging light and obtaining the image of the target in the far field.

Figure 5:
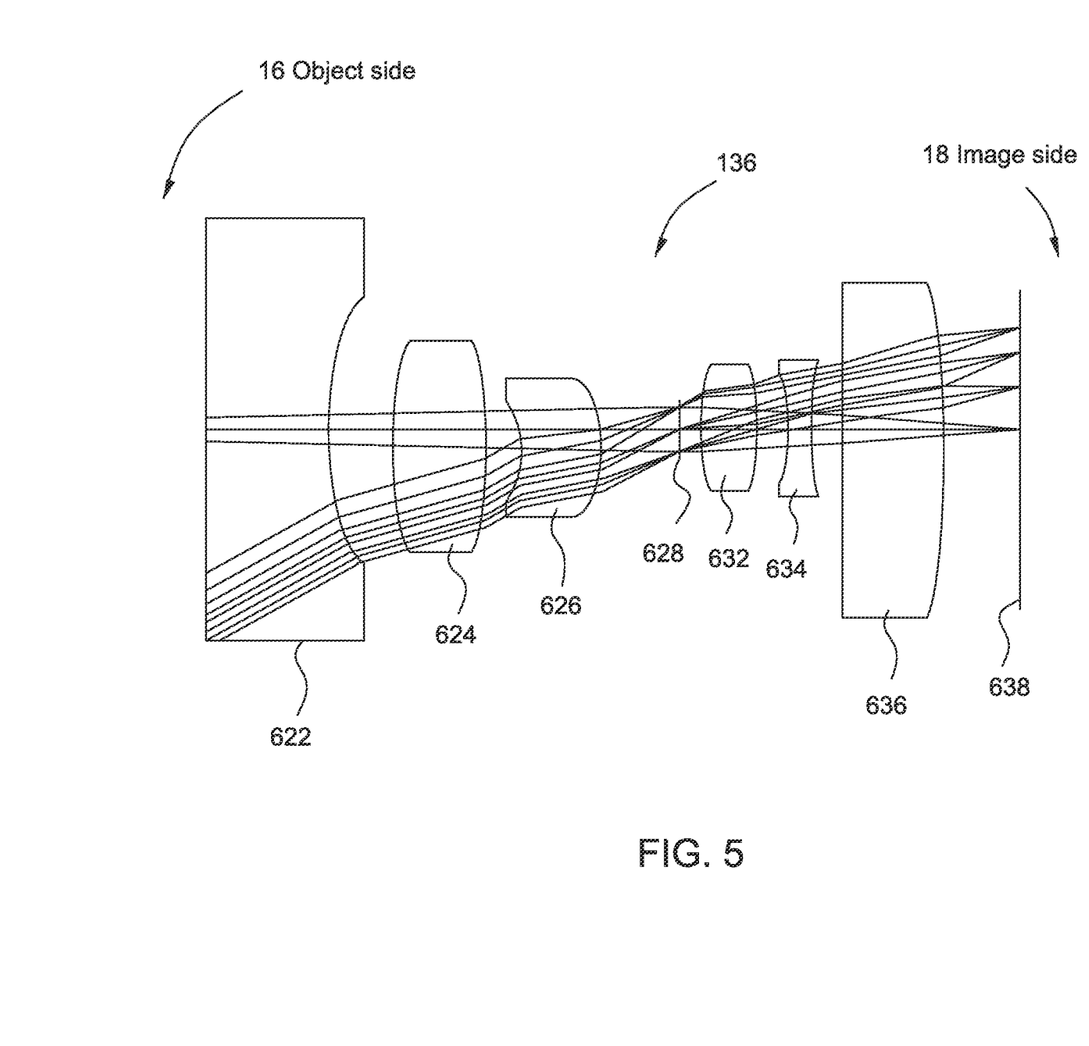
FIG. 5 is a sectional diagram of a lens group of the optical system shown in FIGS. 2 and 3 in accordance with an exemplary embodiment of the present disclosure.

FIG. 5 illustrates a detailed diagram of a lens group 136 of the optical system 130 shown in FIGS. 2 and 3 in accordance with an exemplary embodiment. In the illustrated embodiment, the lens group 136 includes a first lens 622, a second lens 624, a third lens 626, an aperture stop 628, a fourth lens 632, a fifth lens 634, and a sixth lens 636 arranged in an order between an object side 16 and an image side 18. The numerical values of lens group 136 are shown as below in table-1, where r is radius of curvature of each surface, d is distance between adjacent two surfaces along the optical axis, n is the refractive index of the lens, and v is the Abbe number of the lens. In this embodiment, the first lens 622 is a plano-concave lens having a negative refractive power. As used herein, "negative" refers to a lens having the capability of diverging light. The second lens 624 and the fourth lens 632 are both double-convex lenses having positive refractive powers. As used herein, "positive" refers to a lens having the capability of converging light. The third lens 626 is a meniscus (concave-convex) lens having a negative refractive power. The fifth lens 634 is a double-concave lens having a negative refractive power. The sixth lens 636 is a birefringent lens having different refractive powers with respect to light of different polarization states. In one implementation, the aperture stop 628 is positioned between the third lens 626 and the fourth lens 632. In other implementations, the aperture stop 628 may be positioned between two other lenses or may be omitted from the lens group 136. The aperture stop 628 may be a variable aperture stop which is capable of being switched to change its aperture size corresponding to focal length change of the lens group 136 or the optical system 130 to achieve optimized image brightness and depth of field for different fields viewing. In one implementation, the variable aperture stop 628 can be switched to have at least a first size and a second size corresponding to the near field and the far field respectively. For one example, when the target in the near field is to be inspected, the size of variable aperture stop 628 can be switched to have a relatively smaller aperture size. Because near field usually has sufficient illumination, the aperture size of the aperture stop 628 can be reduced to achieve maximum Depth of Field (DOF). For another example, when the target in the far field is to be inspected, the variable aperture stop 628 can be switched to have a relatively larger second aperture size. Because far field usually does not have sufficient illumination, the aperture size of the aperture stop 628 can be enlarged to let more light to pass through the lens group 136 to improve image brightness.

TABLE 1

Numerical value of the lens group 136 shown in FIG. 5

| | | | | |
|---|---|---|---|---|
| First lens 622 | $r_1$ = infinity | $d_1$ = 1.50 mm | $n_1$ = 1.80 | $v_1$ = 39.6 |
| | $r_2$ = 2.312 mm | $d_2$ = 0.64 mm | | |
| Second lens 624 | $r_3$ = 7.186 mm | $d_3$ = 1.50 mm | $n_2$ = 1.78 | $v_2$ = 25.7 |
| | $r_4$ = −5.702 mm | $d_4$ = 0.60 mm | | |
| Third lens 626 | $r_5$ = −2.460 mm | $d_5$ = 1.34 mm | $n_3$ = 1.75 | $v_3$ = 51.0 |
| | $r_6$ = −2.740 mm | $d_6$ = 2.31 mm | | |

TABLE 1-continued

Numerical value of the lens group 136 shown in FIG. 5

| Stop 628 | $r_7$ = infinity | $d_7$ = 0.21 mm | — | — |
|---|---|---|---|---|
| Fourth lens 632 | $r_8$ = 1.9060 mm | $d_8$ = 1.00 mm | $n_4$ = 1.62 | $v_4$ = 60.3 |
| | $r_9$ = −1.500 mm | $d_9$ = 0.20 mm | | |
| Fifth lens 634 | $r_{10}$ = −1.265 mm | $d_{10}$ = 0.50 mm | $n_5$ = 1.78 | $v_5$ = 25.7 |
| | $r_{11}$ = 2.991 mm | $d_{11}$ = 0.31 mm | | |
| Sixth lens 636 | $r_{12}$ = infinity | $d_{12}$ = 1.50 mm | $YVO_4$ | — |
| | $r_{13}$ = −3.9836 mm | $d_{13}$ = 1.96 mm | | |

Figure 6:
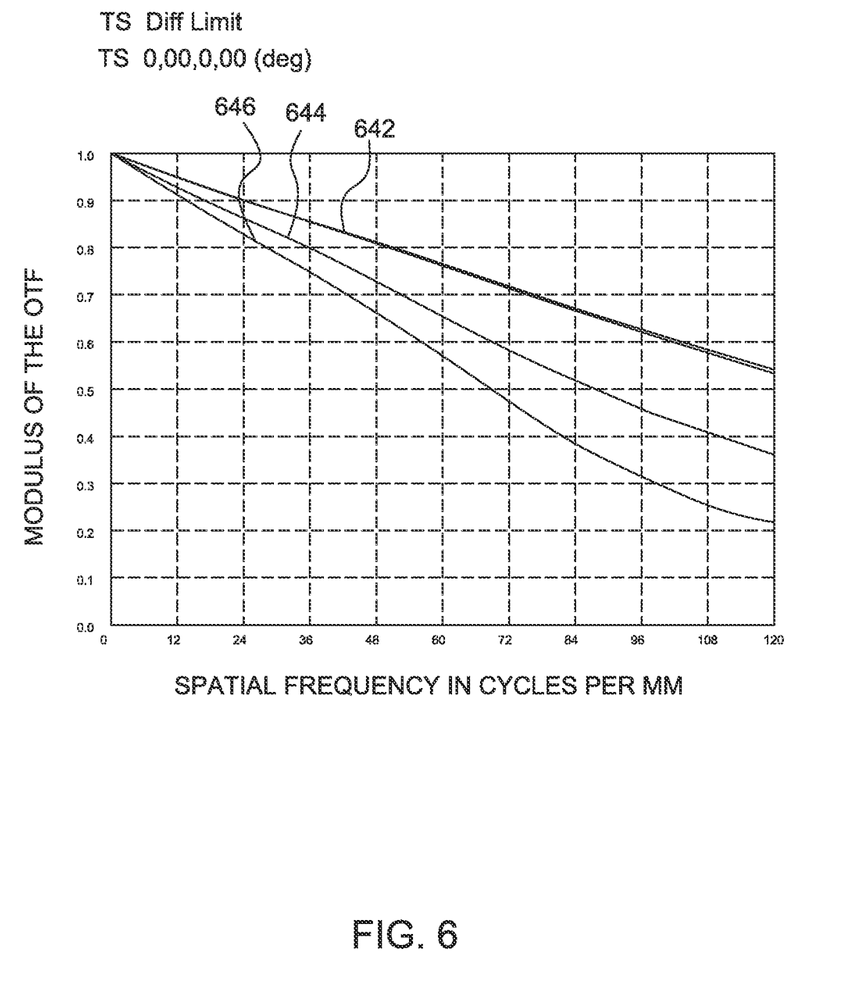
FIGS. 6 and 7 are graphical representations of modulation transfer function (MTF) curves illustrated for evaluating the optical performance of the lens group shown in FIG. 5 in accordance with an exemplary embodiment of the present disclosure, wherein the lens group is switched to different refractive power to capture images of the same target at the same distance in the near field.
Figure 7:
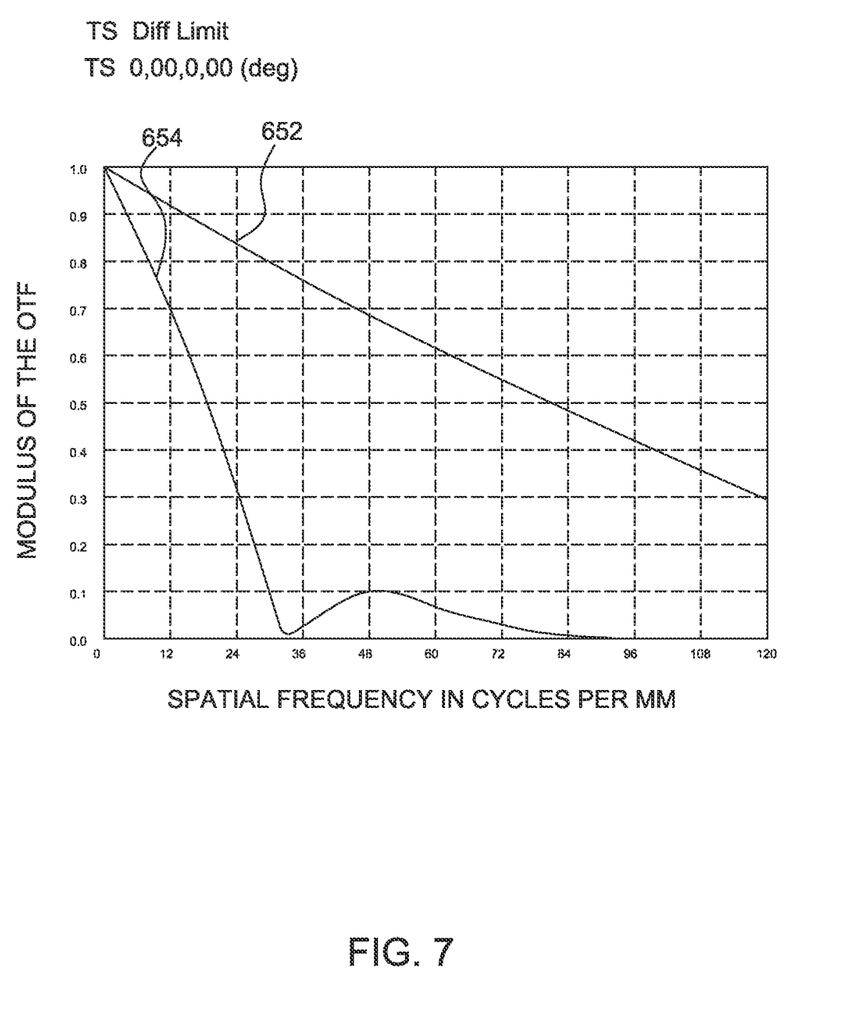
Figure 8:
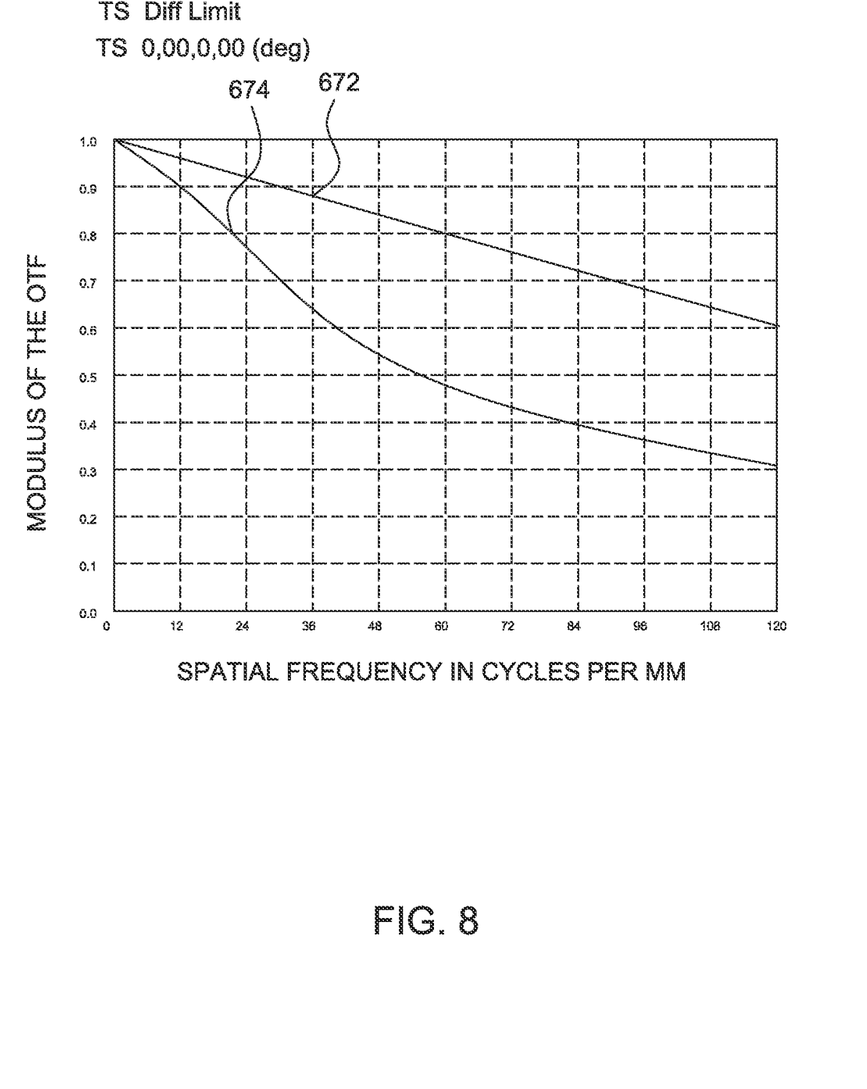
FIGS. 8 and 9 are graphical representations of MTF curves illustrated for evaluating the optical performance of the lens group shown in FIG. 5 in accordance with an exemplary embodiment of the present disclosure, wherein the lens group is configured to be switched to different refractive power to capture images of the same target at the same distance in the far field.
Figure 9:
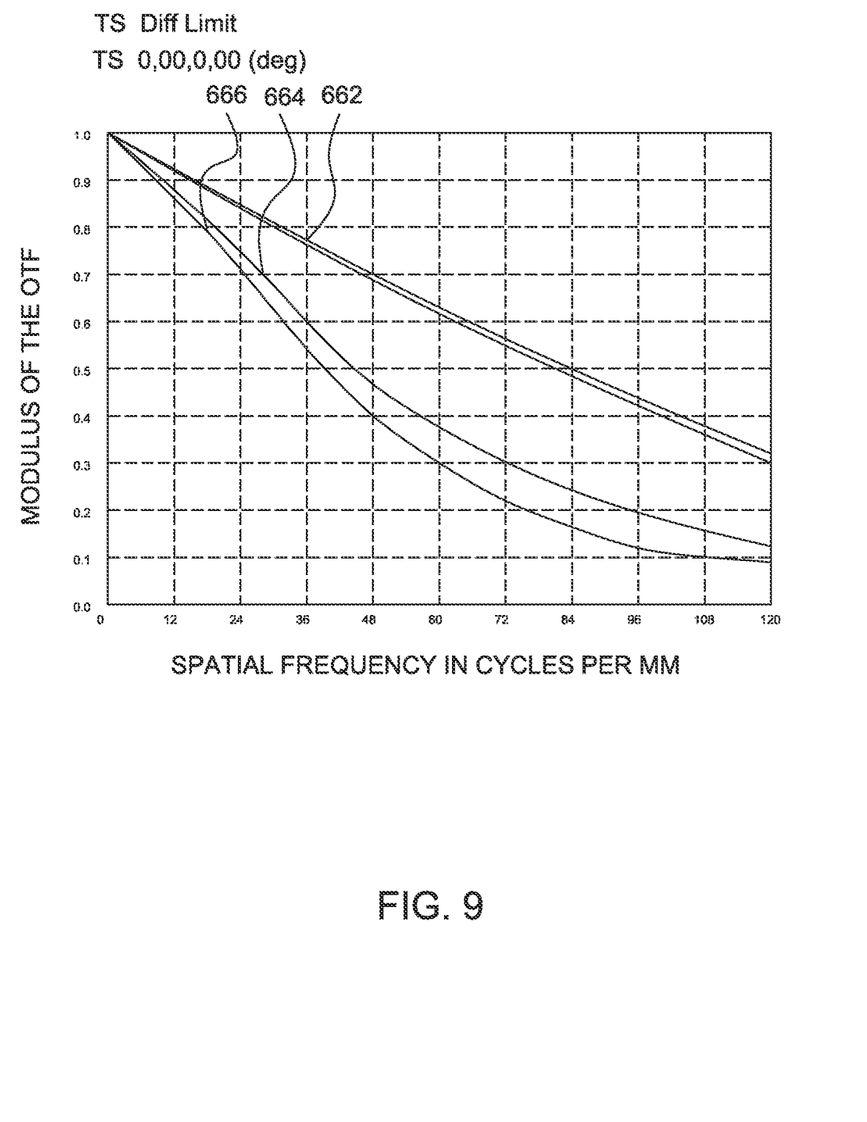

The optical performance of the lens group 136 shown in FIG. 5 can be evaluated by comparing its modulus transfer function (MTF) diagrams both in the near field and the far field. FIGS. 6 and 7 illustrate MTF diagrams of the lens group 136 in the near field. FIGS. 8 and 9 illustrate MTF diagrams of the lens group 136 in the far field. As shown in FIGS. 6-9, each of the MTF diagrams includes a horizontal axis representing spatial frequency in cycles (or line pairs) per millimeter and a vertical axis representing modulus value ranging from 0 to 1. In FIG. 6, the target is positioned at a distance of 20 mm with respect to the optical system 130, and the lens group 136 is set with an F number of 5.8. The MTF diagram is plotted by operating the lens group 136 to converge light (e-beam) with a relatively larger refractive index ($YVO_4$ $n_e$=2.2560 at 532 nm) or shorter focal length. In FIG. 7, the target is positioned at the same distance of 20 mm with respect to the optical system 130, while the lens group 136 is set with an F number of 8.2. The MTF diagram shown in FIG. 7 is plotted by operating the lens group 136 to converge light (o-beam) with a relatively smaller refractive index ($YVO_4$ $n_o$=2.0210 at 532 nm) or longer focal length.

In the MTF diagrams shown in FIGS. 6 and 7, MTF curves 642 and 652 are theoretical curves of a perfect lens group, known as diffraction limited, having the same diameter as the lens group 136 of FIG. 5. A tangential (T) curve 646 and sagittal (S) a curve 644 are also shown in FIG. 6. From FIGS. 6 and 7, it is shown that, at the same spatial frequency, the modulus value of the T curve 646 and the S curve 644 shown in FIG. 6 are larger than that of the MTF curve 654 shown in FIG. 7. Thus, in the near field, even the F number of the lens group 136 is increased (in FIG. 7) to mitigate focal position change caused by switching the optical system 130 with a relatively longer focal length, the image of the target can be formed with good quality by switching the optical system 130 to converge light with a relatively shorter focal length.

Similarly as described above with respect to FIGS. 6 and 7, it can be seen from FIGS. 8 and 9 that it is beneficial to switch the optical system 130 to converge light with a relatively longer focal length, such that the image of the target in the far field can also be formed with good quality. In FIG. 8, the target is positioned at a distance of 250 mm with respect to the optical system 130, and the lens group 136 is set with an F number of 5.3. The MTF diagram is plotted by operating the lens group 136 to converge light (o-beam) with a relatively longer focal length. In FIG. 9, the target is positioned at the same distance of 250 mm with respect to the optical system 130, while the lens group 136 is set with an F number of 7.8. The MTF diagram shown in FIG. 9 is plotted by operating the lens group 136 to converge light (e-beam) with a relatively shorter focal length. From FIGS. 8 and 9, it is shown that, at the same spatial frequency, the modulus value of the MTF curve 674 shown in FIG. 8 are larger than that of the MTF curves 664 and 666 shown in FIG. 9. Thus, in the far field, even the F number of the lens group 136 is increased (in FIG. 9) to mitigate focal position change caused by switching the optical system 130 with a relatively shorter focal length, the image of the target can be formed with good quality by switching the optical system 130 to converge light with a relatively longer focal length.

As described above, the optical system 130 is capable of being switched between at least a first focusing state and a second focusing state. At the first focusing state, the optical system 130 can exhibit a relatively shorter focal length with respect to light having a first polarization state, such that the target positioned in a near field can be imaged. At the second focusing state, the optical system 130 can exhibit a relatively longer focal length with respect to light having a second polarization state, such that the target positioned in the far field can also be imaged. In operation of the inspection device 10 employed with the focal length switchable optical system 130, it is convenient to inspect targets positioned in the near field and far field by switching between the states. In comparison to a traditional inspection device, faster imaging of the targets can be achieved with the focal length of the optical system increased when inspecting targets in the far field. During inspection of the target in the far field, because the longer focal length is used, the aperture size can be increased to achieve lower F number to allow more light to pass through the optical system, such that brighter image of the target can be provided. Moreover, during inspection of the target in the near field, because the shorter focal length is used, the aperture size can be reduced to achieve higher F number to provide maximum Depth of Field.

In case of the target being placed at a distance in an overlapping region of the near field and far field, for the target to be formed with clear images, either the lens group 130 is switched to the first focal length or the second focal length, and the zoom ratio can be expressed by the following equation:

$$Z' = \frac{f_2}{f_1}, \qquad (1)$$

where Z' is the simplified zoom ratio, $f_1$ is the first focal length of the lens group 130, and $f_2$ is the second focal length of the lens group 130. Therefore, when the lens group 130 is switched from a relative shorter first focal length $f_1$ to a relatively longer second focal length $f_2$ to view the same target at the same object distance, the image of the target appears to be enlarged. Likewise, when the lens group 130 is switched from a relatively longer second focal length $f_2$ to a relatively shorter first focal length $f_1$, the image of the target appears to be reduced.

While the invention has been described with reference to exemplary embodiments, it will be understood by those skilled in the art that various changes may be made and equivalents may be substituted for elements thereof without departing from the scope of the embodiments of the invention. In addition, many modifications may be made to adapt a particular situation or material to the teachings of the embodiments of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An optical system configured to visually inspect a target, the target comprising variable positions with respect to the optical system, the optical system comprising:
   a polarizer configured to convert an incident light reflected or diffused from the target into linearly polarized light;
   a light modulating element configured to modulate a polarization state of the linearly polarized light in response to control signals;
   a lens assembly comprising at least one birefringent element, the birefringent element configured to refract the modulated linearly polarized light with a first polarization state under a first refraction index to enable inspection of the target at a first object position with respect to the optical system, and the at least one birefringent element further configured to refract the modulated linearly polarized light with a second polarization state under a second refraction index to enable inspection of the target at a second object position with respect to the optical system;
   a detector configured to detect a position of the target with respect to the optical system, the detector further configured to provide positional signals used for automatically switching the optical system between a first inspection mode and a second inspection mode, wherein in the first inspection mode, the target at a first position with respect to the optical system is inspected; and
   wherein in the second inspection mode, the target at a second position with respect to the optical system is inspected.

2. The optical system of claim 1, wherein the polarizer is configured to generate the linearly polarized light based on optical mechanisms selected from a group consisting of an optical reflection mechanism, an optical refraction mechanism, and an optical absorption mechanism.

3. The optical system of claim 1, wherein the light modulating element is selected from a group consisting of a Faraday rotator, an optoelectric crystal, a wave plate, and a liquid crystal.

4. The optical system of claim 1, wherein the birefringent element comprises a birefringent lens, a birefringent window, or a polarization splitting prism.

5. The optical system of claim 1, wherein the birefringent element comprises a material selected from a group consisting of Calcite, α-BBO Crystal ($BaB_2O_4$), Yttrium orthovanadate, Lithium Niobate, and Quartz.

6. The optical system of claim 1, wherein the birefringent element comprises a birefringent window, the birefringent window comprising a predetermined thickness to provide an optical path change for different states of polarization light passing therethrough and a shift of focal position of the different states of polarization light.

7. The optical system of claim 1, further comprising a variable aperture stop, wherein the variable aperture stop is configured to be switched into at least a first aperture size and a second aperture size corresponding to a first focal length and a second focal length of the lens assembly.

8. An optical system configured to visually inspect a target, the target comprising variable positions with respect to the optical system, the optical system comprising:
   a polarizer configured to convert an incident light reflected or diffused from the target into linearly polarized light;
   a light modulating element configured to modulate a polarization state of the linearly polarized light in response to control signals; and
   a lens assembly comprising at least one birefringent element, the at least one birefringent element configured to refract the modulated linearly polarized light with a first polarization state under a first refraction index to enable inspection of the target at a first object position with respect to the optical system, and the at least one birefringent element further configured to refract the modulated linearly polarized light with a second polarization state under a second refraction index to enable inspection of the target at a second object position with respect to the optical system; and
   a detector configured to detect a position of the target with respect to the optical system, the detector further configured to provide positional signals used for automatically switching the optical system between a first inspection mode and a second inspection mode, wherein in the first inspection mode, the target at a first position with respect to the optical system is inspected;
   wherein in the second inspection mode, the target at a second position with respect to the optical system is inspected; and
   wherein the lens assembly further comprises a first lens with negative refractive power, a second lens with positive refractive power, a third lens with negative refractive power, a fourth lens with positive refractive power, and a fifth lens with negative refractive power, wherein the first lens, the second lens, the third lens, the fourth lens, and the fifth lens are disposed in an order from an object side to an image side of the optical system.

9. An inspection device for inspecting at least a near field target and a far field target, the inspection device comprising:
   a light source, the light source configured to emit light to illuminate the near field target or the far field target; and
   an optical system configured to receive light reflected or diffused from the near field target or the far field target, convert the reflected or diffused light to linearly polarized light;
   modulate a polarization state of the linearly polarized light, and refract the modulated linearly polarized light under either a first refractive power when the near field target is to be inspected or a second refractive power when the far field target is to be inspected;
   wherein the optical system is further configured to:
      detect a position of either the near field target or the far field target; and
      provide positional signals used for automatically switching the optical system between a first state where the near field target is to be inspected and a second state where the far field target is to be inspected,
   wherein when the near field target and the far field target are positioned in an overlapping region of near field and far field, a first image of the near field target is zoomed in a ratio with respect to a second image of the far field target.

10. The inspection device of claim 9, wherein the optical system comprises one or more birefringent elements for exhibiting a first refractive index with respect to the modulated linearly polarized light incident thereto with a first polarization state and for exhibiting a second refractive index with respect to the modulated linearly polarized light incident thereto with a second polarization state.

11. The inspection device of claim 9, wherein in inspecting the near field target, the optical system is further configured to reduce an aperture size of an aperture stop to allow less light pass therethrough to achieve maximum depth of field; and wherein in inspecting the far field target, the optical system is further configured to increase the aperture size of the aperture stop to allow more light pass therethrough to increase image brightness.

12. A method for inspecting a target, the target comprising variable positions with respect to an optical system employed in an inspection device, the method comprising:

receiving light reflected or diffused from the target;
converting the received light into linearly polarized light;
modulating a polarization state of the linearly polarized light in response to control signals;
refracting the modulated linearly polarized light using at least one refractive element, wherein the at least one refractive element is configured to refract different polarization states under different refractive indices;
detecting a position of the target with respect to the optical system; and
automatically switching the optical system between a first inspection mode and a second inspection mode based on the detected position of the target with respect to the optical system;
wherein in the first inspection mode, the optical system is configured to inspect the target in a near field, the target in a first position with respect to the optical system; and
wherein in the second inspection mode, the optical system is configured to inspect the target in a far field, the target in a second position with respect to the optical system.

13. The method of claim 12, further comprising:

zooming an image of the target by switching the polarization state of the linearly polarized light, wherein the target is positioned in an overlapping region of the near field and the far field.

14. The method of claim 12, further comprising:

adjusting an aperture stop to have a first aperture size corresponding to a first polarization state of the linearly polarized light or have a second aperture size corresponding to a second polarization state of the linearly polarized light.

15. The method of claim 12, further including operating the optical system comprising:
a polarizer configured to convert the light reflected or diffused from the target to the linearly polarized light;
a light modulating element configured to selectively modulate the polarization state of the linearly polarized light; and
a lens group configured to converge a first polarized light and a second polarized light modulated by the light modulating element to an imager, the lens group comprising the at least one refractive element, the refractive element configured to refract the first polarized light under a first focal length to form a first image of the target on the imager, and the birefringent element further configured to refract the second polarized light under a second focal length to form a second image of the target on the imager;
wherein the optical system is operated so that the second image is zoomed to a ratio with respect to the first image, and the ratio is determined at least based on the first focal length and the second focal length.

16. The method of claim 15, wherein the lens group further comprises an aperture stop, the method further comprising switching the aperture stop into at least a first aperture size and a second aperture size corresponding to a first focal length and a second focal length of the lens group.

* * * * *

UNITED STATES PATENT AND TRADEMARK OFFICE
CERTIFICATE OF CORRECTION

PATENT NO. : 9,188,543 B2  
APPLICATION NO. : 13/448691  
DATED : November 17, 2015  
INVENTOR(S) : Li et al.

Page 1 of 1

It is certified that error appears in the above-identified patent and that said Letters Patent is hereby corrected as shown below:

IN THE SPECIFICATION

In Column 8, Line 1, delete "1—can" and insert -- 10 can --, therefor.

In Column 10, Line 43, delete "lens group 130" and insert -- lens group 136 --, therefor.

In Column 10, Line 53, delete "lens group 130," and insert -- lens group 136, --, therefor.

In Column 10, Line 54, delete "lens group 130." and insert -- lens group 136. --, therefor.

In Column 10, Line 54, delete "lens group 130" and insert -- lens group 136 --, therefor.

In Column 10, Line 58, delete "lens group 130" and insert -- lens group 136 --, therefor.

Signed and Sealed this  
Twenty-ninth Day of March, 2016

Michelle K. Lee  
*Director of the United States Patent and Trademark Office*